United States Patent [19]

Beppu et al.

[11] Patent Number: 5,580,782

[45] Date of Patent: Dec. 3, 1996

[54] ACETIC ACID BACTERIUM, PLASMID DERIVED FROM SAID BACTERIUM AND SHUTTLE VECTORS CONSTRUCTED WITH SAID PLASMID

[75] Inventors: Teruhiko Beppu, Tokyo; Naoto Tonouchi, Omiya; Sueharu Horinouchi, Tokyo; Takayasu Tsuchida, Yokohama, all of Japan

[73] Assignee: Bio-Polymer Research Co., Ltd., Kawasaki, Japan

[21] Appl. No.: 331,488

[22] PCT Filed: Feb. 28, 1994

[86] PCT No.: PCT/JP94/00315

§ 371 Date: Dec. 23, 1994

§ 102(e) Date: Dec. 23, 1994

[87] PCT Pub. No.: WO94/20626

PCT Pub. Date: Sep. 15, 1994

[30] Foreign Application Priority Data

Mar. 8, 1993 [JP] Japan .................................... 5-046845

[51] Int. Cl.⁶ .............................. C12N 1/20; C12N 15/74; C12N 15/00
[52] U.S. Cl. .................................... 435/252.1; 435/320.1; 435/172.3
[58] Field of Search ........................... 435/172.3, 320.1, 435/252.1

[56] References Cited

PUBLICATIONS

Tonouchi et al., Biosci. Biotech. Biochem. 58(10):1899–1901 (1994).
Fukaya et al., Agric. Biol. Chem. 49(5):1349–1355 (1985).
Agric. Biol. Chem. 49(7), pp. 2083–2090, 1985, Masahiro Fukaya, et al., "Construction of New Shuttle Vectors for Acetobacter".
Agric. Biol. Chem. 49 (4), pp. 1011–1017, 1985, Hajime Okumura, et al., "Construction of Plasmid Vectors and a Genetic Transformation System for Acetobacter Aceti".

*Primary Examiner*—Nancy T. Vogel
*Attorney, Agent, or Firm*—Oblon, Spivak, McClelland, Maier & Neustadt, P.C.

[57] ABSTRACT

Acetobacter sp. strain BPR 2001, an endogeneous plasmid named pAH4 derived from said strain as well as shuttle vectors constructed from said plasmid and an *E. coli*-derived plasmid are disclosed.

These shuttle vectors can be advantageously used for gene recombination of cellulose-producing acetic acid bacteria.

6 Claims, 2 Drawing Sheets

Construction of pSA19 and pSA7

Construction of pK5

ACETIC ACID BACTERIUM, PLASMID DERIVED FROM SAID BACTERIUM AND SHUTTLE VECTORS CONSTRUCTED WITH SAID PLASMID

FIELD OF THE INVENTION

This invention relates to Acetobacter sp. strain BPR 2001, a plasmid named pAH4 carried by said strain and shuttle vectors constructed from said plasmid and an *E. coli*-derived plasmid.

DISCUSSION OF THE BACKGROUND

Microorganisms belonging to *Acetobacter xylinum* have been long known as acetic acid bacteria that produce bacterial cellulose. Recently, bacterial cellulose produced by acetic acid bacteria including *Acetobacter xylinum* has received attention as material for, for example, medical pads or loudspeaker diaphragms because its cellulose microfibrils are more uniformly oriented as compared with plant-derived cellulose so that it is homogeneous and mechanically strong.

However, the cellulose productivity of acetic acid bacteria is low. Therefore, some attempts were made to improve the productivity by varying incubation conditions or introducing mutation. In addition to these conventional means, the modern recombinant gene technology is also being applied in the studies to improve the productivity. In order to bring about gene recombination in cellulose-producing acetic acid bacteria, it is necessary to develop, first of all, a host-vector system for the object bacterium.

It has been known that such microorganisms produce not only cellulose but also acetan which is a water-soluble polysaccharide. In view of the utility of acetan as starting material for food-based thickeners and various chemical products, it is also useful to develop such a host-vector system. Seven vector plasmids carried by *Acetobacter aceti* subsp. *xylinum* IFO 3288 were already reported (JPA1-199580).

Plasmids carried by acetic acid bacteria were also reported in JPW4-503456 and Proc. Natl. Acad. Sci. USA, Vol. 87, pp. 8130–8134 (1990).

On the other hand, it would be very convenient for gene recombination of acetic acid bacterial plasmids, if plasmid vectors which can replicate not only in acetic acid bacteria but also other host cells such as *E. coli* (hereinafter referred to as "shuttle vectors") are available.

Such shuttle vectors were previously reported in, for example, JPA1-199580 cited above and BIOTECHNOLOGY LETTERS, Vol. 14, No. 7 (July, 1922), pp. 539–542.

SUMMARY OF THE INVENTION

In this state of arts, the present inventors have studied to provide a plasmid derived from a novel cellulose-producing acetic acid bacterium and novel shuttle vectors constructed from said plasmid and an *E. coli*-derived plasmid, and succeeded in newly isolating a cellulose-producing bacterium, which was classified as an Acetobacter according to the method described in Bergey's Manual of Systematic Bacteriology and designated as Acetobacter sp. strain BPR 2001. The Acetobacter sp. strain BPR 2001 is taxonomically characterized as a rod-shaped, gram-negative, non-spore-forming and aerobic bacterium, and proves to be positive for catalase, negative for oxidase, positive for acetic acid production from ethanol, positive for oxidation of acetate and positive for oxidation of lactate. The inventors have further found that this strain is novel and carries a novel plasmid, and thus completed this invention.

Accordingly, this invention provides Acetobacter sp. strain BPR 2001 and endogenous plasmids derived from said strain, especially pAH4.

DETAILED DESCRIPTION OF THE PREFERRED EMBODIMENTS

Figure 1:
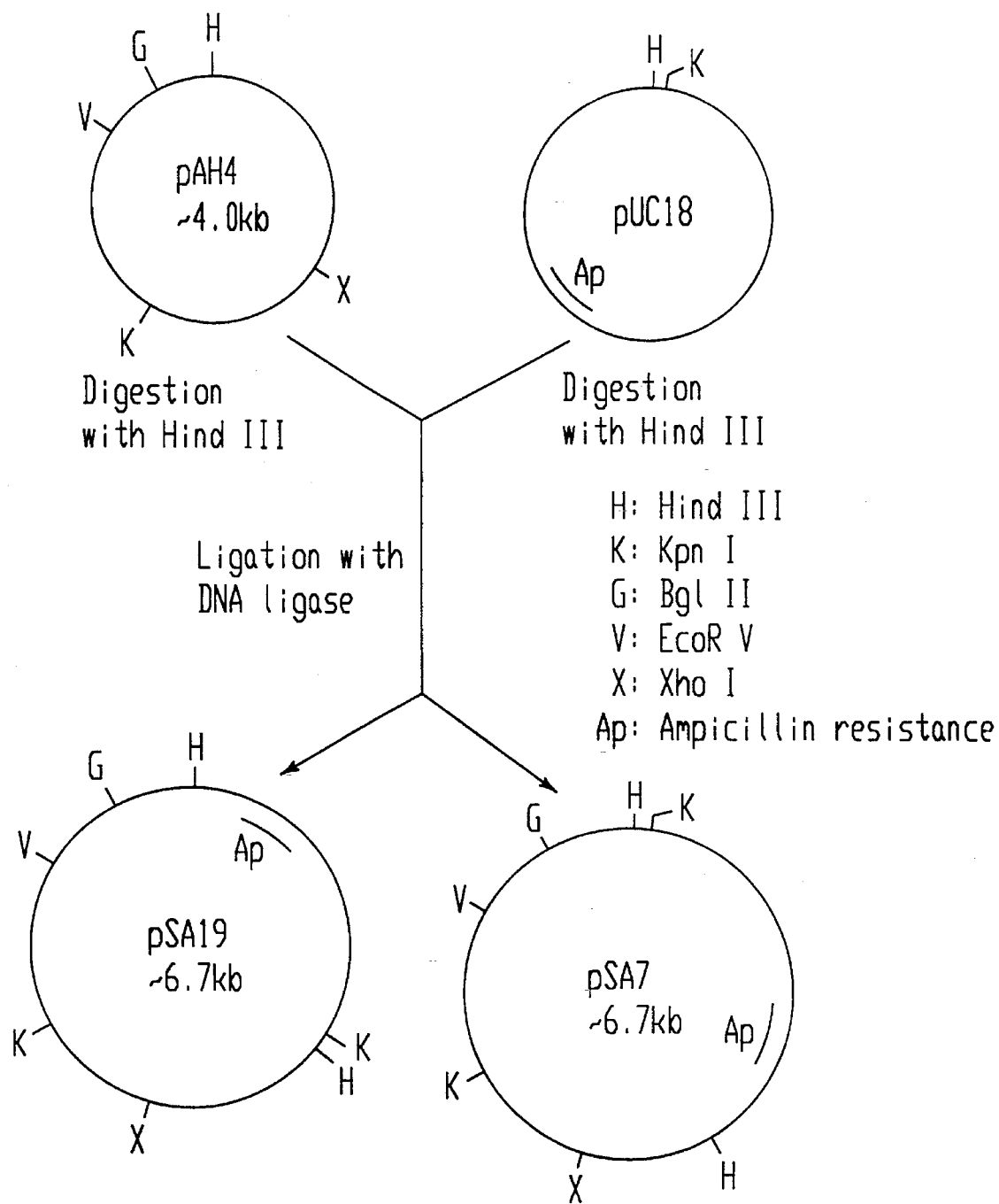
FIG. 1 illustrates the construction of pSA19 and pSA7.
Figure 2:
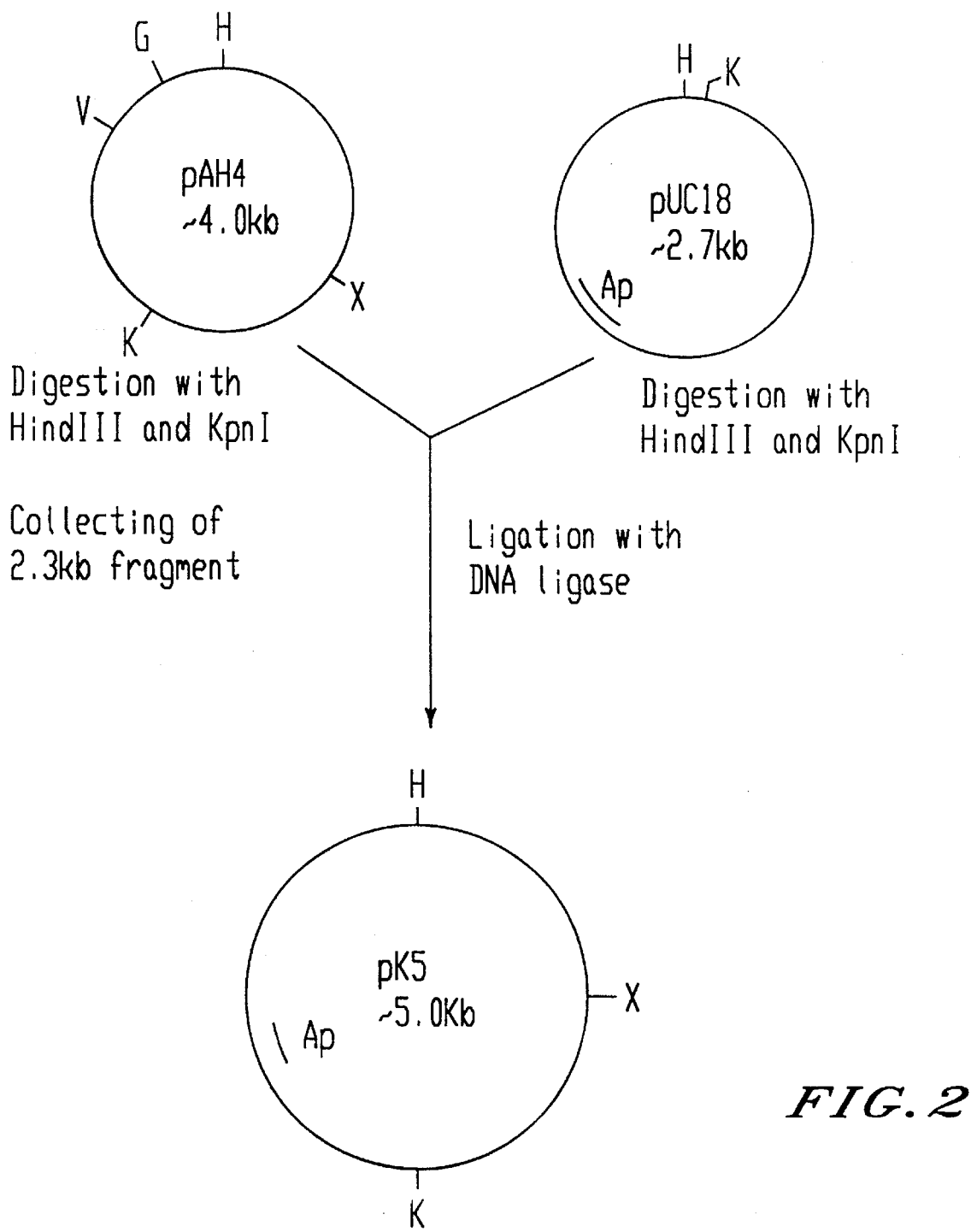
FIG. 2 illustrates the construction of pK5.

This plasmid pAH4 has a relatively small size of about 4.0 kb, and restriction endonuclease sites which make it suitable for use as vector, as shown in Example 1.

Further, the plasmid pAH4 of this invention has the base sequence of about 4002 bp shown as SEQ ID NO: 1 in the SEQUENCE LISTING annexed.

This invention also provides shuttle vectors constructed from said plasmid and an *E. coli*-derived plasmid such as pUC18.

Typical examples of such shuttle vectors include pSA19, pSA7 and pK5, which are all able to replicate either in the host cells of cellulose-producing acetic acid bacteria or those of *E. coli*, and therefore constitute very useful plasmids as vectors for gene recombination of cellulose-producing acetic acid bacteria.

The Acetobacter sp. strain BPR 2001 was deposited on Feb. 24, 1993 in the Patent Microorganism Deposition Center of the National Institute of Bioscience and Human-Technology, Agency of Industrial Science and Technology, Ministry of International Trade and Industry, 1–3 Higashi I-chime, Tsukuba-shi, Ibaraki-ken, 505, Japan (Accession No. FERM P-13466), and then transferred to the deposit under the Budapest Treaty on Feb. 7, 1994 (Accession No. FERM BP-4545).

This invention will now be explained in detail by reference to examples.

EXAMPLES (1) Isolation and Purification of the Plasmid

A culture of the strain BPR 2001 was incubated in YPD medium (0.5% yeast extract, 0.2% polypeptone, and 3% glucose, pH 6.5) and filtered through gauze to remove the cellulose, and then the cells were harvested by centrifugation. The plamid DNA was extracted from the cells by the conventional alkalilysis method (Birnboim, H. C. and J. Doly; Nuc. Acids Res., Vol. 7, page 1513, 1979) and purified by agarose gel electrophoresis. This gave a plasmid of about 4 kb, which was designated as pAH4.

pAH4 was treated with several restriction endonucleases (commercially available from Takara Shuzo Co., Ltd.) to draw the following restriction endonuclease map of the plasmid.

(2) Determination of the Base Sequence

The base sequence of pAH4 was determined by the dideoxy chain termination method by Sanger et al. (Sanger, F. and A. R. Coulson; J. Mol. Biol., Vol. 94, page 441, 1975).

This base sequence is shown as SEQ ID NO: 1 in the SEQUENCE LISTING annexed.

(3) Construction of Shuttle Vectors pAH4 was digested with the restriction endonuclease Hind III. This digest was mixed with a digest of the *E. coli* vector plasmid pUC18 (commercially available from Takara Shuzo Co., Ltd.), and the mixture was treated with a DNA ligase (commercially available from Takara Shuzo Co., Ltd.). The ligation product was transformed into the *E. coli* strain JM105 (commercially available from Takara Shuzo Co., Ltd.) by the calcium chloride method (Norgard, M. V., K. Keem and J. J. Monahan; Gene, Vol. 3, page 279, 1978). The resulting ampicillin-resistant strains were screened for the presence of chimeric plasmids of pAH4 and pUC18, and such chimeric plasmids were designated as pSA19 and pSA7.

Further, pAH4 was digested with the restriction endonucleases Hind III and KpnI, and a fragment of about 2.3 kb was collected by agarose gel electrophoresis. This fragment and the Hind III-KpnI digest of pUC18 were mixed and ligated to each other with DNA ligase, and the ligation product was transformed into the *E. coli* strain JM105. The resulting ampicillin-resistant strains were screened for the presence of chimeric plasmids, and such a plasmid was designated as pK5.

The *E. coli* JM105 strains harboring these plasmids, namely pSA19, pSA7 and pK5, were also deposited in the above Patent Microorganism Deposition Center on Feb. 24, 1993 under Accession Nos. FERM P-13469, FERM P-13468 and FERM P-13467, and then transferred to the deposit under the Budapest Treaty on Feb. 7, 1994 under Accession Nos. FERM BP-4548, FERM BP-4547 and FERM BP-4546, respectively.

(4) Transformation of Acetobacter sp. Strain BPR 2001 with each Chimeric Plasmid Cultures of the strain BPR 2001 were incubated in YPD medium containing 0.1% cellulase and transformed by electroporation. Cells were harvested by centrifugation, washed with a 10% sucrose solution, then resuspended in a 10% sucrose solution, and mixed with the plasmid DNA. The mixture was subjected to 20 electric pulses of 1400 V with a "Shimazu cell fusion apparatus SSH-10" (Shimazu Corp.). All of the plasmids pSA19, pSA7 and pK5 yielded ampicillin-resistant strains. Plasmid isolation from these strains by the method described above resulted in the same plasmids as introduced.

(5) Construction of the Plasmid pSABSC and Expression of Cellulase Genes

The plasmid pBRC501 (Biosci. Biotech. Biochem., Vol. 57, pp. 260–264 (1993)) in which a *Bacillus subtilis* neutral cellulase gene is expressed by *E. coli* lactose promoter and the plasmid pSA19 were digested with the restriction endonucleases SacI and BamHI (both commercially available from Takara Shuzo Co., Ltd.). The object DNA fragments were separated and collected by agarose gel electrophoresis, and ligated to each other with T4DNA ligase (commercially available from Takara Shuzo Co., Ltd.) to give a plasmid named pSABSC.

The strain BPR 2001 was transformed with this pSABSC by the electroporation method described above, to give a strain with said gene introduced therein.

A culture of this strain was incubated in CSL fructose medium. The cellulase activity of the phosphate buffer cell extract was determined by the method described in J. Bacteriology, Vol. 158, pp. 503–506 (1984) (DNS method). The specific activity was 0.141 U/mg protein, which proved that the cellulase gene had been properly introduced in the strain BPR 2001 and expressed by using pSA19.

(6) Production of Cellulose and Acetan by Acetobacter sp. Strain BPR 2001

1) Seed Culture

A 750 ml Roux flask containing 100 ml of a culture medium including 40 g/l sucrose, 3 g/l $KH_2PO_4$, 2.4 g/l $MgSO_4 \cdot 7H_2O$, 1 g/l $(NH_4)_2SO_4$, 20 g/l corn steep liquor, and 0.01% defoamer was inoculated with. 1 ml of the stock culture solution and statically incubated at 28° C. for 3 days.

2) Main Culture

After seed incubation, the Roux flask was thoroughly shaken. Then, the contents of the flask were filtered through gauze under aseptic conditions. A 300 ml baffled Erlenmeyer flask containing 67.5 ml of the above culture medium was inoculated with 7.5 ml of the filtrate. Incubation was continued for 4 days in a shaker-incubator (BR-3000L: manufactured by Taitec Co.) at an amplitude of 2 cm, rotation speed of 180 rpm and a temperature of 28° C.

3) Determination of BC

After washed with water to remove the medium components, the solids in each flask were treated in 1% NaOH solution at 110° C. for 20 minutes to remove the cells. The cellulose was washed with water until the washings approximated the neutrality, and then dried under vacuum at 80° C. to determine for the dry weight. On the 2nd, 3rd and 4th day of incubation, 1.90 g/l, 2.90 g/l and 3.37 g/l of cellulose had accumulated in the medium, respectively. During this incubation, 3.00 g/l of water-soluble acetan had accumulated in the medium on the 4th day.

---

We claim:

1. An endogenous plasmid isolated from Acetobacter sp. strain BPR 2001 (FERM BP-4545).

2. The plasmid according to claim 1 which is pAH4 and which has the base sequence shown as SEQ ID NO: 1.

3. A shuttle vector which has been constructed from a plasmid according to claim 1 or claim 2, and an *E. coli*-derived plasmid.

4. The shuttle vector according to claim 3, wherein said *E. coli*-derived plasmid is pUC18.

5. The shuttle vector according to claim 4, which is any one of pSA19, pSA7 and pK5.

6. Acetobacter sp. strain BPR 2001 (FERM BP-4545).

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4002 base pairs
( B ) TYPE: nucleic acid ( C ) STRANDEDNESS: single
( D ) TOPOLOGY: circular ( i i ) MOLECULE TYPE: other nucleic acid
( A ) DESCRIPTION: /desc ="plasmid"

( x i ) SEQUENCE DESCRIPTION: SEQ ID NO:1:

| | | | | | |
|---|---|---|---|---|---|
| AAGCTTCTGG | CGGGCGGATT | CCTGTTCAGC | CCGCTTTTGC | GCCTCGCGTG | TTCCCGCGCC | 60 |
| AATCGCTCCA | TTATGGCCCG | CTGCCGTCCT | GCCTCTCCTG | CTCCTTCCGC | TCGATGGCAT | 120 |
| CCCGACCCAC | CTCGTCGGCC | AGATCGGCGA | ACCAGTCCAT | CAGGTCTTCC | GCTGCCTGCT | 180 |
| GAACCTTGGC | GATGGCCTGT | TCCGCGCTTT | CGATGATATG | GCGCAGGGCT | TTCGCAATCC | 240 |
| CGTTCTTCTC | GGCGGCATCC | GCATTTGCCC | TGGCACGGTA | GGTTCTGGGT | TCATACTCCC | 300 |
| GACCTTCCTG | CTCGGCCTGA | TGCGCGGCCT | TGCGTTCGAC | CGCCGTGCTG | TGCGGCCCGA | 360 |
| GATGGACGCC | GGGCACAACC | TCGACACCCT | GCCGCTCATA | ACTCCGGTGA | TCGACGCGGG | 420 |
| CGGTCTGTCC | GGCCCGCTCT | AGCAGCCTGT | CGGGTTGGGC | ATTTTGCGGC | TGATAACGCC | 480 |
| AAGGCTGACC | TGGCTTATGC | TGCCTGAAGC | CGCGCCATTC | TTTTACAGTT | GTATGCGAGA | 540 |
| GCAACGAGTG | TCCATTCGGT | CGTGACTTTT | GCAAGGCCAC | GCAGGCTGAA | TTTTCTGAAG | 600 |
| CCCATGATGC | TTTTGATAAT | TCCAAAGACC | GGCTCCACGG | TCTGTTTTCG | TCGTCTGTAA | 660 |
| AGATCTCCGG | CTTCTGTAGT | TTCCAGCCTG | TCCTTCATGG | CAAGCCGCCA | GGGTTCGGTT | 720 |
| ATCCGGCGTG | GCTCCCTTTC | TGCGGGCCGG | GGTCGGAAGT | CGTAAGGTCT | GCGGGCACAG | 780 |
| GGCCGTCCAA | TGGCGACCAG | CGGATCAATG | CCCTTTTCCC | GCAGTTTCCG | GACCGCCTGC | 840 |
| CCGCTGGCGT | AACCGGTATC | GGCGAGCACT | GTCTTTGGGA | GACCGATTGT | GTCTTCCATC | 900 |
| GACAGCACCG | TGTCGGCAAA | GGACGGCGCA | TCCGCTGATG | TGGCGACAAC | GTCGGTTGTC | 960 |
| ACGATCAACT | GGCTGCCTTC | GGCGCACACC | ACGGCCTGGG | CATTGTAAGC | CTGCCGGAAC | 1020 |
| TCGTGGGCGT | CCGAACGCCG | CATGAGGCGG | CTGTCGGGAT | CGGTCAGACT | GATCTGTCGG | 1080 |
| TCGGGTGGTG | GTTCATCACT | CGGGCGGTTT | GGGCGCCCGG | CCGCGACGCC | CTGTTTTCGC | 1140 |
| ATCATAAGCG | GCTTTCTTCT | TCTCGTAGGC | CGGTCGCGCC | GTTTCAGCCT | GCGCCTTCGC | 1200 |
| ATCAGCTTCC | AGCCGGGCGC | AGGCTTCGTC | AGCTTCTTTC | AGCGTTTCCC | GCCGGGCAAG | 1260 |
| CTCTTCCGGC | AATGCTGCGG | ATCTCTGTCT | GTGACGTCCG | CATCTCCGCC | TGGTCCATCA | 1320 |
| GTTTCGCGAT | ATCCACAGCC | AGCTGTTCGC | GCACGCCTGA | TCCGGTCGTA | GCGCACCGAA | 1380 |
| CGGTATTTCG | ATGCGTCAGC | ATCGATTTTC | GTGCCGTCGA | TCGACACCAC | GCCCAGACGC | 1440 |
| AGCAGACCCG | TCTCGCGCGC | CAGAAGCAGG | ACCTGCGCAA | ATGCAGCTTC | AATGGCTGTC | 1500 |
| CGGTTCGTCC | GGCGGAAGGT | CGCAATCGTA | TCATGATCCG | GATGCAGGTT | CGCCGCCACG | 1560 |
| AATCGCACCC | CGATGTCGCG | ATATGTCGCC | CGCTCGATCC | GGCGTGAGGA | AAACAACCCG | 1620 |
| TTCGCATAGC | TGAAGATCAG | AAGGGCCAGC | ATCAGGCGCG | GATGATACTG | CGCCTTGCCT | 1680 |
| CCCGTGCGCA | CTGGCACGCA | GAACGCACTC | ATCGGAACCC | GCTCAACGGC | GGCTACAATG | 1740 |
| AAATGCGCCA | TATCATCAGC | AGGAAGCCAC | GACTTCAGAT | CAGGCGGCAG | AAGATACGGC | 1800 |
| TGAGACCGGT | CAAACGGGAT | GAAGCTGCTC | ATCACACCAC | CTTACAATCG | CCCCCTTCAC | 1860 |
| AGGGTACCCC | AACCCGACAG | GCTGCTAGAA | CCGCCGTAGA | AGCGTCCGAG | GCATTCGCAG | 1920 |
| TGTCGAAACC | CCGCCTAATG | ATCTGGACGG | CCCTCTGTGC | CTTCCTGCTG | GTCTCTGGCG | 1980 |
| GGTGGTTGGC | AGCGTTCTGG | GTAGGCAGAC | ACGATGGCTG | GGCCGCTGGT | CAGGTCGATG | 2040 |
| GCAGACAGGA | AGCCCTCACC | GCCAATGCCG | CCGCGTCATG | GGCGAATACC | ACCAGCGGGA | 2100 |
| AGATGGCCAA | GCAACTGGAT | GACCTCGGCA | ACCTTCAACC | TTTGGCGACT | TGCAACGTCC | 2160 |

```
CCGGATTCTC CATCCAGAAG GGGGAAAAGG GTGTTCGCTG GTGTGTGGTT GCTGGAACAG 2220
ACGGGCAGTT CCACGGGTGG GCGATGCCCT GACGAACCCT TCCCTCTTCC TGAGCAATTC 2280
GGAAGATCAA TTTCCTCTAG CCTAACACGT CGAAAACGGG AGTTTTCCAC CAAAAAGAG  2340
AGACCTACAG AGAGATTAAA TTTCTTTCTC TTTCTTAACC ATAGTCAACC CGCGCGAGAC 2400
TGCGGAAAAA TGCTTGTAAT AGGTTACAGG ATATGTAACC CAGAAGTTAC AGGGGCTGTA 2460
ACCTATTAGC CCGTTATCAA CAGGGGTGCG AGATGTCCCG GATTGTCAGA CTGACCACCA 2520
AGCGGCAAAT GGCCGACCAG CAGGCCGCAG CTACCATTGC CGAACAACTG GAACTCATCA 2580
CTCCGGAAAT GCTGGAAGGC GCTCCGGGAG ACCTGAAACT GTTGCTGTCA CGGGCTATCT 2640
ACAGCGCACA AAAGCAATCG CGCCCGAACA CCGAAGGACT TTGGCCGGGA GTTTCACCAT 2700
GATTAGCCGC GACCAGACGA AACTTGTGTG GGATGCCATC CGCGCCCTTC CGCCAGAAGA 2760
TCGCCCCCAG CAGGTACGTC ACGCCTTCGA TCTGGCCTTG CTGTCACTGC GACAGGATAC 2820
CGGCGAAATC ATGATGCGCC GTGATGAACT TGCCGAAGAA ATCGGCTGTT CTCCGCAGAA 2880
CGTCAGCCAA ATTATGGGCG TTCTCGAGCG TATGGGTGCC GTCCGTCGAA CCCGCCAAAA 2940
GGTGCCGGGG ATCAGAGGAC CGGGTGTGGC AATATATTAC ATCAACCCGC ATGTCGGCTG 3000
GAATGGCTCT CTAGATGCTC GCAAGGCACA GGCTGAAGAA ATCCATCCGC CGGTACAGCT 3060
TGAGCTTCTG CAAGGGGGAG CCAAATGAGT TCCCGTAGAA GCAGTAGAGC ACAGGGCACC 3120
AATCCAAAAG CTCTAGGATT AAACCCTAGA GCACTTGGAT TAAGTCCTAA ACAATTAGGA 3180
ATTAGCCCCC GTCAGCTCGG GATTAGCCCT AAGCAACTCG CAAAAAGAG  GCAAATCATG 3240
ACCGACCTAT CCGACGAACT GGCCGCCAAA CGGGCGGCAA TCCGTGCAGC CCGCGAATGC 3300
ACAGAACCGT CGCTGTCTGC GGCGGAGGCT ATCGCCTTGC TGGAATCCGA TCTGGTTATG 3360
GTTCAGGCAG CTATCGACGC TCTACACGCC GAGGAACGCC GTGCAGGTTG AGTGGTCGAA 3420
GCTGGCCCGT TCTGATGCGG AAGCAATCAG AGCCTACCTG TTGGATCGAA ACCCATACGC 3480
AGCTAAGCGA ATTTACTCC GTCTGATCGA TGCGACAAAA GACTTGGCAA TGTTCCCGAG 3540
CATCGGTCGG ATAGGGCTGG ACGGCACCCG CGAATGGGTC GTCGCCCAGC CCTACGTTCT 3600
GCTCTACGAA GTCAATGAAA TGGCCGGAAT CGTTAAAATC CTGCGTGTTT GGCACAGCGC 3660
CCAAGACCGC TGAATAGCCT CTAACGCCTT CGCCGGGGGC GGGGTACAC AGGCACTAGA 3720
CCTAATCCCA AAACCCGGTG TCAAATTGGC TATTATCCAA GGCGTTGCAA AACAATTCTT 3780
AAGTAATGAA ATATTTTTAT TGACAACATA TGAAAAAAT CGTATAAATA ATATTATGCG 3840
GCCATGGTGA AATTTGGTAA ACACATATAA TTTGGAATTA TAGATACATT TAAGAGAGTA 3900
TTTGAGGGTT CAAGTTCCTC TGGCCGCACC ATATAAATCT CAAAATACTT AGCGTCGCCT 3960
TCCTCCCGGC CCTTTACGTC CGCCTGTGAA GCCCTCGTCG AT                     4002
```